United States Patent [19]

Behner et al.

[11] Patent Number: 5,342,847
[45] Date of Patent: * Aug. 30, 1994

[54] SPECIFIC 1,4-DIHYDROPYRIDINE-3,5-DICARBOXYLIC ACID ESTER AND ITS PHARMACEUTICAL USE

[75] Inventors: Otto Behner; Hartmund Wollweber; Siegfried Goldmann, all of Wuppertal; Bruno Rosen, Wülfrath; Siegfried Zaiss, Wuppertal, all of Fed. Rep. of Germany

[73] Assignee: Bayer Aktiengesellschaft, Leverkusen, Fed. Rep. of Germany

[*] Notice: The portion of the term of this patent subsequent to Aug. 10, 2010 has been disclaimed.

[21] Appl. No.: 1,017

[22] Filed: Jan. 16, 1993

[30] Foreign Application Priority Data

Jan. 14, 1992 [DE] Fed. Rep. of Germany ....... 4200714

[51] Int. Cl.$^5$ ................. C07D 211/86; A61K 31/455
[52] U.S. Cl. ..................................... 514/356; 546/321
[58] Field of Search ......................... 546/321; 514/356

[56] References Cited

U.S. PATENT DOCUMENTS

| 3,883,543 | 5/1975 | Bossert | 546/321 |
| 3,956,341 | 5/1976 | Loev | 546/321 |
| 4,707,486 | 11/1987 | Flockerzi et al. | 514/318 |
| 4,780,538 | 10/1988 | Pitzenberger et al. | 546/321 |
| 4,975,440 | 12/1990 | Flockerzi et al. | 514/318 |

FOREIGN PATENT DOCUMENTS

| 0239186 | 9/1987 | European Pat. Off. . |
| 0451654 | 10/1991 | European Pat. Off. . |
| 2210667 | 9/1973 | Fed. Rep. of Germany . |

OTHER PUBLICATIONS

H. Dornow and W. Sassenberg, Liebigs Ann. Chem. 602, 14 (1957) Beilstein 7 (3), 1013.

*Primary Examiner*—Jane T. Fan
*Attorney, Agent, or Firm*—Sprung Horn Kramer & Woods

[57] ABSTRACT

The invention relates to the new dimethyl 2,6-dimethyl-1-n-propyl-4-(trifluoromethylphenyl)-1,4-dihydropyridine-3-dicarboxylate, a process for its preparation and its use as a medicament in ischaemic diseases which are associated with disorders of the microcirculation. This action can occur both in the peripheral and in the cerebral vascular system.

3 Claims, No Drawings

SPECIFIC 1,4-DIHYDROPYRIDINE-3,5-DICARBOXYLIC ACID ESTER AND ITS PHARMACEUTICAL USE

The invention relates to the new dimethyl 2,6-dimethyl-1-n-propyl-4-(4-trifluoromethylphenyl) 1,4-dihydropyridine-3,5-dicarboxylate, a process for its preparation and its use as a medicament in ischaemic diseases which are associated with disorders of the microcirculation. This action can occur both in the peripheral and in the cerebral vascular system.

It is already known that 1,4-dihydropyridinedicarboxylic acid esters have a calcium-antagonistic or calcium-agonistic action, and can thus be employed as vessel- and circulation-influencing agents [cf. German Offenlegungsschrift 2,506,987; German Offenlegungsschrift 2,210,667].

EP 240,828 also describes hypotensive 1,4-dihydropyridines with haemorheological properties.

The present invention relates to the new dimethyl 2,6-dimethyl-1-n-propyl-4-(4-trifluoromethylphenyl)-1,4-dihydropyridine-3,5-dicarboxylate of the formula (I)

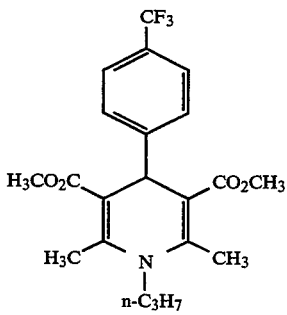

which surprisingly has a potent haemorheological action and improves the circulation, in particular the microcirculation, and at the same time has a lack of effect on blood pressure. It is thus particularly suitable for use in the control of acute and chronic ischaemic disorders.

The compound of the formula (I) according to the invention can be prepared by customary methods, for example, by a process in which

[A] methyl 2-(4-trifluoromethylbenzylidene) acetoacetate of the formula (II)

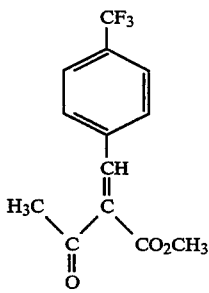

is reacted either directly with methyl 3-n-propylaminocrotonate, or
with methyl acetoacetate and n-propylamine hydrochloride,
in inert solvents, if appropriate in the presence of a base/acid,
or

[B] 4-trifluoromethylbenzaldehyde of the formula (III)

$$\text{(III)}$$

is reacted either with methyl acetoacetate and n-propylamine hydrochloride or n-propylamine and pyridine hydrochloride respectively in pyridine,
or

[C] first, under a protective gas atmosphere, Lewis acids, preferably titanium tetrachloride, are treated with methyl 3-n-propylaminocrotonate in inert solvents using a base, preferably piperidine, and then 4-trifluoromethylbenzaldehyde of the formula (III) is added,
or

[D] dimethyl 2,6-dimethyl-4-(4-trifluoromethylphenyl)-1,4-dihydropyridine-3,5-dicarboxylate of the formula (IV)

$$\text{(IV)}$$

is reacted with alkylating agents, preferably n-propyl iodide or n-propyl trifluoromethanesulphonate, in inert solvents and in the presence of a base.

The process according to the invention can be illustrated by way of example by the following reaction scheme:

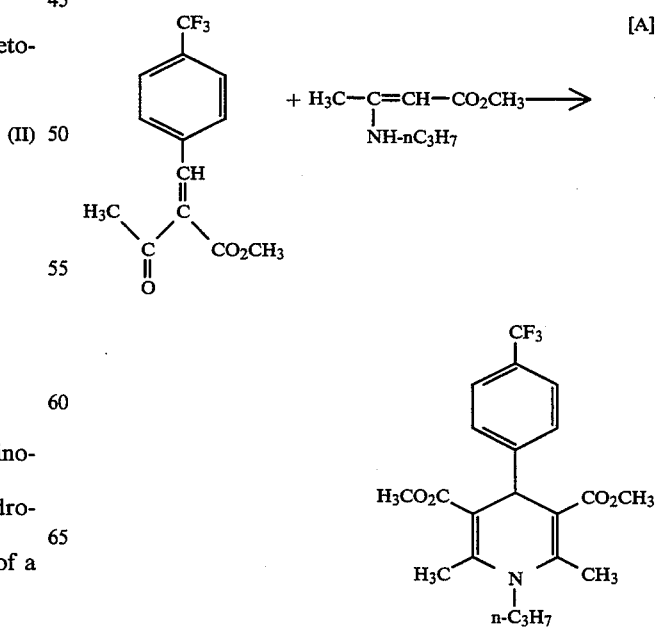

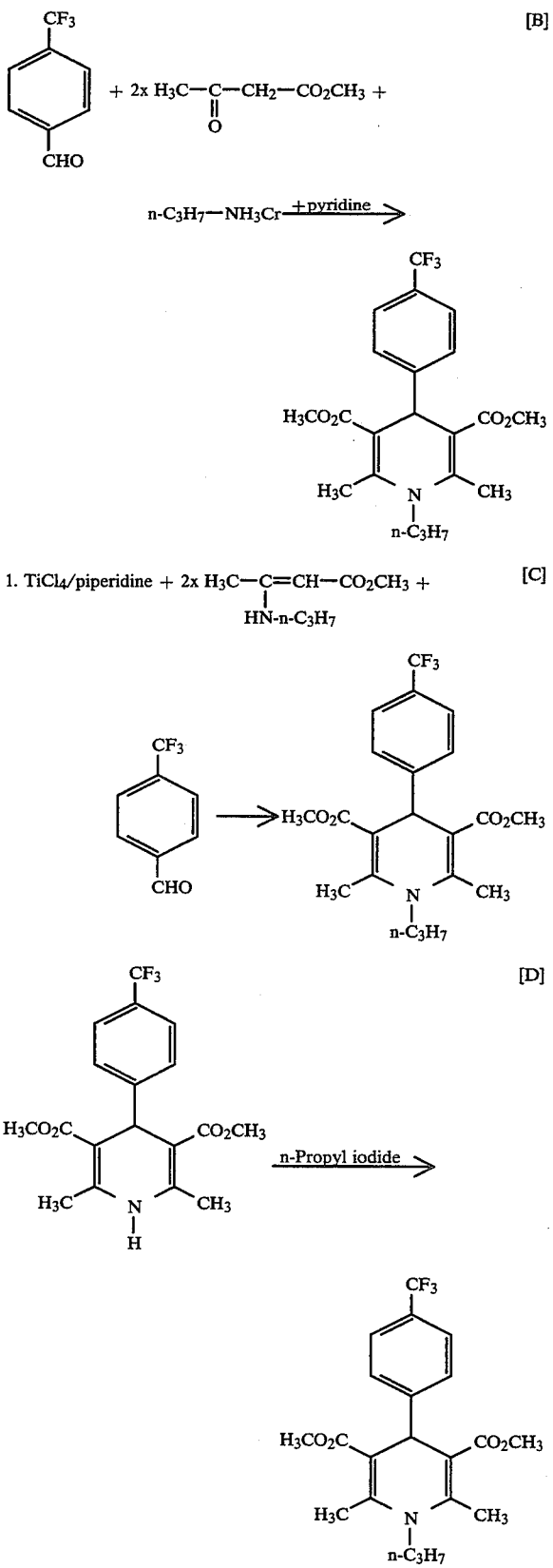

Possible solvents are water or organic solvents which do not change under the reaction conditions. These preferably include alcohols such as methanol, ethanol, propanol, isopropanol, butanol, ethers such as diethyl ether, dioxane, tetrahydrofuran, glycol monomethyl ether or glycol dimethyl ether, or amides such as dimethylformamide, dimethylacetamide or hexamethylphosphoramide, or glacial acetic acid, dimethyl sulphoxide, acetonitrile or pyridine. 1,2-Dimethoxyethane, butanol and pyridine are preferred.

Depending on the individual process steps, bases which can be employed are hydrides such as sodium hydride, alkali metal or alkaline earth metal hydroxides, such as, for example, sodium hydroxide or potassium hydroxide, alkoxides, such as potassium tert-butoxide, or pyridine. Sodium hydride and pyridine are preferred. Acids employed are in general hydrochloric acid or sulphuric acid.

The reaction temperatures can be varied within a relatively wide range. In general, the reaction is carried out between $+10°$ C. and $+150°$ C., preferably between $+20°$ C. and $+100°$ C., in particular at the boiling point of the respective solvent.

The reaction can be carried out at normal pressure, but also at elevated or reduced pressure. In general, it is carried out at normal pressure.

When carrying out process variants A, B, C and D according to the invention, any desired ratio of the substances participating in the reaction can be used. In general, however, the reaction is carried out with molar amounts of the reactants. The substances according to the invention are preferably isolated and purified by distilling off the solvent in vacuo and recrystallising the residue, which may be obtained in crystalline form only after ice-cooling, from a suitable solvent. In some cases, it may be necessary to purify the compounds according to the invention by chromatography.

The compound of the formula (II) is known and can be prepared by a customary method [cf. H. Dornow and W. Sassenberg, Liebigs Ann. Chem. 602, 14 (1957)].

4-Trifluoromethylbenzaldehyde (III) is also known [cf. Bellstein 7 (3), 1013].

Alkylating agents which can be employed in the process are, for example, n-propyl halides, preferably n-propyl iodide, n-propyl trifluoromethanesulphonate or di-n-propyl sulphate.

The alkylation is carried out in the abovementioned solvents at temperatures from $0°$ C. to $+150°$ C., preferably at room temperatures up to $+100°$ C., at normal pressure.

The new compound shows an unforeseeable, useful spectrum of pharmacological action.

Combined with a lack of vasal and blood pressure effects in a dose range up to at least 10 mg/kg i.v. and 30 mg/kg p.o., it increases the circulation, in particular the microcirculation, by affecting the deformability of the erythrocytes and the inhibition of the activation and adhesion of the leucocytes.

The lack of effect on blood pressure is determined in the following models, which are typical for dihydropyridines; in SH rats after p.o. administration by measurement in the tail artery (Riva Rocci method) and in anaesthetised Wistar rats after i.v. administration. (Measurement was carried out by means of a catheter in the carotid artery). This compound is designated as having a lack of effect on blood pressure, since it does not decrease the blood pressure in the two test models at the given dose.

The difference between the therapeutic dose and a blood pressure action is at least a factor of 100.

The compound according to the invention can therefore be employed for the production of medicaments for the treatment of acute and chronic ischaemic disorders, such as intermittent claudication, myocardial infarct, cerebral infarct and also of reperfusion damage and shock.

The following in vitro and in vivo tests show the interesting actions of the specifically selected compound according to the invention.

I) Erythrocyte Function

The deformability of erythrocytes plays a substantial role in the origin and the course of acute or chronic ischaemic disorders. They determine the viscosity of the blood and thus its distribution in the microcirculation. The tests used detect various determinants:

Test a) detects the antihaemolytic action of the substances ($ED_{50}$, mol/l). In this test, calcium-laden erythrocytes are pressed through small pores under high shearing stresses so that haemoglobin is released and measured as an expression of their haemolysis. The decrease in haemoglobin release is the quantity measured.

Test b) detects the viscosity of erythrocyte suspensions in glass capillaries (25 μm diameter) at low shearing stresses occurring in vessel areas behind a stenosie. Increasing the extracellular calcium increases the viscosity.

a) Antihaemolytic Action in Erythrocytes

Normal erythrocytes become haemolytic under high shearing stresses. The haemolysis of calcium-laden cells is particularly pronounced. This measure of mechanical stability is used for substance characterisation. The quantity measured is the concentration of free haemoglobin in the medium.

b) Viscosity in Glass Capillaries

The biophysical interactions of erythrocytes relevant for the circulation can be investigated in glass capillaries (diameter 20–30 μm). The resulting viscosity depends on the condition of the cells. In the case of calcium loading the viscosity increases. The percentage improvement in the viscosity relative to a damaged, but untreated control at 0.7 Pa is given. The test dose is $10^{-8}$ g/ml.

TABLE I

| Example No. | Effect (%) |
| --- | --- |
| Compound (I) according to the invention | 190 |

II) Leucocyte Function

The microcirculation can be directly observed in the hamster cheek pouch model. Quantities measured are leucocyte adhesion and also vessel diameter and erythrocyte sedimentation rate. Adhesion was quantified under ischaemic and non-ischaemic test conditions. Under nonischaemic conditions, the adhesion is quantified in the area of small venules, under ischaemic conditions (10 min circulation stop) in small arterioles. The results of the control experiments are adjusted to 100%. The test dose selected is in each case 0.1 mg/kg i.v., the results are decreases in % of the control. Surprisingly, it appeared that under ischaemic conditions the substance still acted at 0.03 mg/kg i.v. This is particularly favourable for the indications desired.

TABLE II

| Example No. | Non-ischaemic control = 100% | Ischaemic control = 100% |
| --- | --- | --- |
| Compound (I) according to the invention | 55% | 37% |

III) Blood Pressure

Clinical knowledge shows that antiischaemic actions of dihydropyridines are frequently masked by a vasodilatation. It was therefore the aim to find blood pressure-inactive (i.e. difference between haemorheological action and hypotensive action $\geq 10$ ) DHPs. The following Table shows the doses at which a blood pressure fall occurs on p.o. administration (SH rat) or i.v. administration (anaesthetised Wistar rat).

TABLE III

| Example No. | p.o. (mg/kg) | i.v. (mg/kg) |
| --- | --- | --- |
| Compound (I) according to the invention | >30 | >10 |

The Table shows that, in comparison with model II, the difference between the therapeutic action and blood pressure action (i.v.) is at least 100.

The new active substance can be converted in a known manner into the customary formulations, such as tablets, coated tablets, pills, granules, aerosols, syrups, emulsions, suspensions and solutions, using inert, non-toxic, pharmaceutically suitable excipients or solvents. In this case, the therapeutically active compound should in each case be present in a concentration of about 0.5 to 90% by weight of the total mixture, i.e. in amounts which are sufficient to achieve the dosage range indicated.

The formulations are prepared, for example, by extending the active substances with solvents and/or excipients, if appropriate using emulsifiers and/or dispersants, where, for example, when using water as a diluent, organic solvents can optionally be used as auxiliary solvents.

Administration is carried out in a customary manner, preferably orally or parenterally, in particular perlingually or intravenously.

In general, it has proven advantageous on intravenous administration to administer amounts of about 0,001 to 1 mg/kg, preferably about 0.01 to 0.5 mg/kg of body weight, to achieve effective results, and on oral administration the dosage is about 0.01 to 20 mg/kg, preferably 0.1 to 10 mg/kg of body weight.

In spite of this, it may sometimes be necessary to deviate from the amounts mentioned, to be precise depending on the body weight or on the type of application route, on individual behaviour towards the medicament, the manner of its formulation and the point or interval at which administration takes place. Thus, in some cases it may be sufficient to manage with less than the abovementioned minimum amount, while in other cases the upper limit mentioned must be exceeded. In the case of the administration of relatively large amounts, it may be advisable to divide these into several individual doses over the course of the day.

PREPARATION EXAMPLES

Example 1

Dimethyl 2,6-dimethyl-1-n-propyl-4-(4-trifluoromethylphenyl)-1,4-dihydropyridine-3,5-dicarboxylate

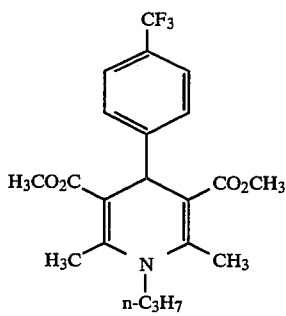

(Process D):

1) 2.95 g (0.008 mol) of dimethyl 2,6-dimethyl-4-(4-trifluoromethylphenyl)1,4-dihydropyridine 3,5-dicarboxylate are dissolved in 25 ml of 1,2-dimethoxyethane, and treated with 0.30 g (0.01 mol) of 80% strength sodium hydride and, after 30 min, with 1.70 g (0.01 mol) of n-propyl iodide. The mixture is stirred at room temperature for 3 hours, neutralised with dilute hydrochloric acid and evaporated in vacuo. The residue is purified by 15 chromatography on silica gel (methylene chloride). Yield=1.02 g (31.0% of theory). Melting point: 102°–104° C.

(Process D):

2) Under argon, 0.3 g (0.01 mol) of 80% strength sodium hydride in 50 ml of dimethylformamide (p.a.) is treated at 0° C. with 1.84 g (0.005 mol) of dimethyl 2,6-dimethyl-4-(4-trifluoromethylphenyl)-1,4-dihydropyridine-3,5-dicarboxylate. A solution of 1.92 g (0.01 mol) of n-propyl trifluoromethanesulphonate in 30 ml of methylene chloride (prepared from trifluoromethanesulphonic anhydride and n-propanol in methylene chloride in the presence of equivalent amounts of pyridine) is then slowly added and the mixture is stirred for 1 h at 0° C. After treating with water, it is extracted with methylene chloride, dried over sodium sulphate and evaporated. The residue is purified by chromatography on silica gel using methylene chloride. 1.16 g (56.6% of theory) are obtained. M.p.: 100°–103° C.

(Process B):

3) A mixture of 5.22 g (0.03 mol) of 4-trifluoromethylbenzaldehyde, 7.04 g (0.06 mol) of methyl acetoacetate and 2.87 g (0.03 mol) of n-propylamine hydrochloride [or 1.78 g (0.03 mol) of n-propylamine and 3.47 g (0.03 mol) of pyridine hydrochloride] is stirred under reflux for 20 hours in 20 ml of pyridine. After distilling off the pyridine, the mixture is partitioned between water and methylene chloride, and the organic phase is washed with water, dried over sodium sulphate and evaporated. The residue is recrystallised from methanol. M.p.: 102°–104° C. Yield: 3.1 g (25.1% of theory)

Process C:

4) Under nitrogen protection, 0.55 ml (5 mmol) of titanium tetrachloride, then 1 ml (10 mmol) of piperidine are added to 20 ml of toluene and the mixture is stirred for 5 min. After the dropwise addition of 3.14 g (20 mmol) of methyl 3-n-propylaminocrotonate, 1.36 ml (10 mmol) of 4-trifluoromethylphenylbenzaldehyde are added and the mixture is stirred at room temperature for 3 hours. For working-up, 100 ml of 5% strength hydrochloric acid are added and the organic phase is taken up with ethyl acetate, and the ethyl acetate solution is washed successively with 5% hydrochloric acid and with sodium bicarbonate solution. After drying the ethyl acetate solution over sodium sulphate, evaporating and stirring the residue in n-heptane, 1.59 g (38.7% of theory) are obtained. M.p.: 100°–102° C.

Process A:

5) 3.72 g (0,039 mol) of n-propylamine hydrochloride are added to a solution of 3.9 g (0.03 mol) of methyl acetoacetate and 8.16 g (0.03 mol) of methyl 2-(4-trifluoromethylbenzylidene)-acetoacetate in 50 ml of pyridine and the mixture is heated under reflux for 5 hours. The reaction product is concentrated in vacuo, the residue is taken up in methylene chloride and water, the aqueous phase is separated off, and the methylene chloride solution is dried over sodium sulphate and evaporated. The residue is purified by chromatography on silica gel using methylene chloride as the solvent. After dissolving and allowing to recrystallise from n-heptane, 1.93 g (15.6% of theory) are obtained. M.p.: 102°–104° C.

We claim:

1. The compound dimethyl 2,6-dimethyl-1-n-propyl-4-(4trifluoromethylphenyl) 1,4-dihydropyridine-3,5-dicarboxylate of the formula (I)

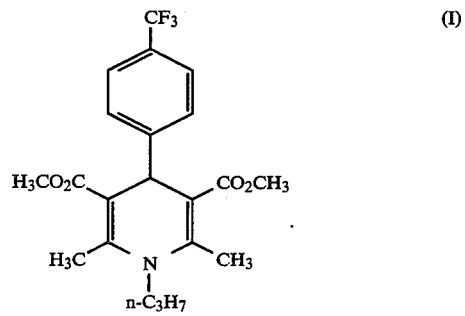

2. A composition for treating ischemic diseases which comprises an amount effective therefor of the compound 2,6-dimethyl-1-n-propyl-4-(4-trifluoromethylphenyl) 1,4-dihydropyridine-3,5-dicarboxylate and a pharmaceutically acceptable diluent.

3. A method of treating ischemic diseases which are associated with disorders of the microcirculation which comprises administering to such patient an amount effective therefore of the compound 2,6-dimethyl-1-n-propyl-4-(4-trifluoromethylphenyl) 1,4-dihydropyridine-3,5-dicarboxylate.

* * * * *